(12) United States Patent
Getek

(10) Patent No.: US 6,406,418 B1
(45) Date of Patent: Jun. 18, 2002

(54) MAGNETIC DRESS BELT

(76) Inventor: Robert F. Getek, 321 SE. 15th Ave., Pompano Beach, FL (US) 33060

(*) Notice: Subject to any disclaimer, the term of this patent is extended or adjusted under 35 U.S.C. 154(b) by 0 days.

(21) Appl. No.: 09/495,085

(22) Filed: Jan. 31, 2000

Related U.S. Application Data

(60) Provisional application No. 60/118,256, filed on Feb. 2, 1999.

(51) Int. Cl.⁷ ................................ A61N 1/00
(52) U.S. Cl. ................................ 600/15
(58) Field of Search .............. 600/15, 9, 10, 600/11, 12, 13, 14; 607/96, 114; 602/13

(56) References Cited

U.S. PATENT DOCUMENTS

| | | | | |
|---|---|---|---|---|
| 4,480,596 A | * | 11/1984 | Shumiyashu | 600/15 |
| 5,832,879 A | * | 11/1998 | Pitzen | 600/15 |
| 5,993,375 A | * | 11/1999 | Engel | 600/15 |
| 6,217,505 B1 | * | 4/2001 | Sakuma | 600/15 |

* cited by examiner

*Primary Examiner*—Kevin Shaver
*Assistant Examiner*—Brian Szmal
(74) *Attorney, Agent, or Firm*—Malin, Haley & DiMaggio, P.A.

(57) ABSTRACT

A magnetic dress belt having one or more magnets embedded therein for providing magnetic therapy to the user's lower back. The magnets are situated along a material such as foam, which is sandwiched between two leather strappings. All three components are sewn together to form the magnetic belt. The belt appears, from the outside, to be a conventional leather belt. The belt may be used as a conventional dress belt while providing continuous and long-lasting unidirectional or multidirectional magnetic penetration to the user's lower back.

6 Claims, 3 Drawing Sheets

MAGNETIC DRESS BELT

This application claims the benefit of the Feb. 2, 1999 filing date of Provisional Patent Application Serial No. 60/118,256.

BACKGROUND OF THE INVENTION

1. Field of the Invention

The invention relates to dress belts having hidden magnets and more specifically to a leather dress belt with a plurality of small magnet discs imbedded therein to provide the user with around-the-clock magnetic therapy while allowing the user to maintain a professional appearance.

2. Description of Related Art

Belts providing therapeutic benefits are well know in the art. Weightlifters and other athletes often use support belts during athletic events or while training. Support belts of this type may be worn under clothes or over an athletic shirt.

However, these belts are often unsightly and uncomfortable to the user. They are impractical in that they cannot be worn for a great length of time due to the user's discomfort. Therefore, they supply only a limited therapeutic benefit due to their restricted use.

While it is uncomfortable to wear these belts, it is also unsightly. Those who must wear suits or dress pants every day to work cannot wear large, bulky belts of this type. Wearing these types of belts over dress clothes would be unsightly. Bulky belts of this type worn under clothing would surely be visible.

While some belts provide mere lumbar support to the user's lower back, they fall short of providing actual and continuous therapeutic benefit.

Accordingly, what is needed in the art is a leather dress belt, capable of being worn with dress clothes and suits, having one or more magnets embedded within the belt, wherein the magnets provide unidirectional or multidirectional penetration to a user's back, yet cannot be seen through the belt.

It is, therefore, to the effective resolution of the aforementioned problems and shortcomings of the prior art that the present invention is directed.

BRIEF SUMMARY OF THE INVENTION

The present invention comprises a flexible dress belt to be worn around a user's waist. It includes one or more magnets embedded within the belt wherein said magnets provide magnetic therapy to the wearer's lower back. The magnets remain completely hidden from site within the belt.

The magnets reside between a pair of leather strappings which comprise the belt itself. Between the strappings is material, such as foam. The small magnets are situated within this material.

The number of magnets may vary, but generally, approximately 20 magnets are used. These magnets may be any standard magnet in the industry, such as Neodymium or ceramic.

Therefore, it is an object of this invention to provide a dress belt with one or more magnets embedded therein, which provides round-the-clock therapeutic relief to the wearer.

It is another object of the present invention to provide the user with a leather dress belt that completely conceals the magnets therein, giving the appearance that the belt is a typical leather dress belt.

In accordance with these and other objects which will become apparent hereinafter, the instant invention will now be described with particular reference to the accompanying drawings.

DETAILED DESCRIPTION OF THE INVENTION

The present invention will now be described in detail utilizing one embodiment for example.

Figure 1:
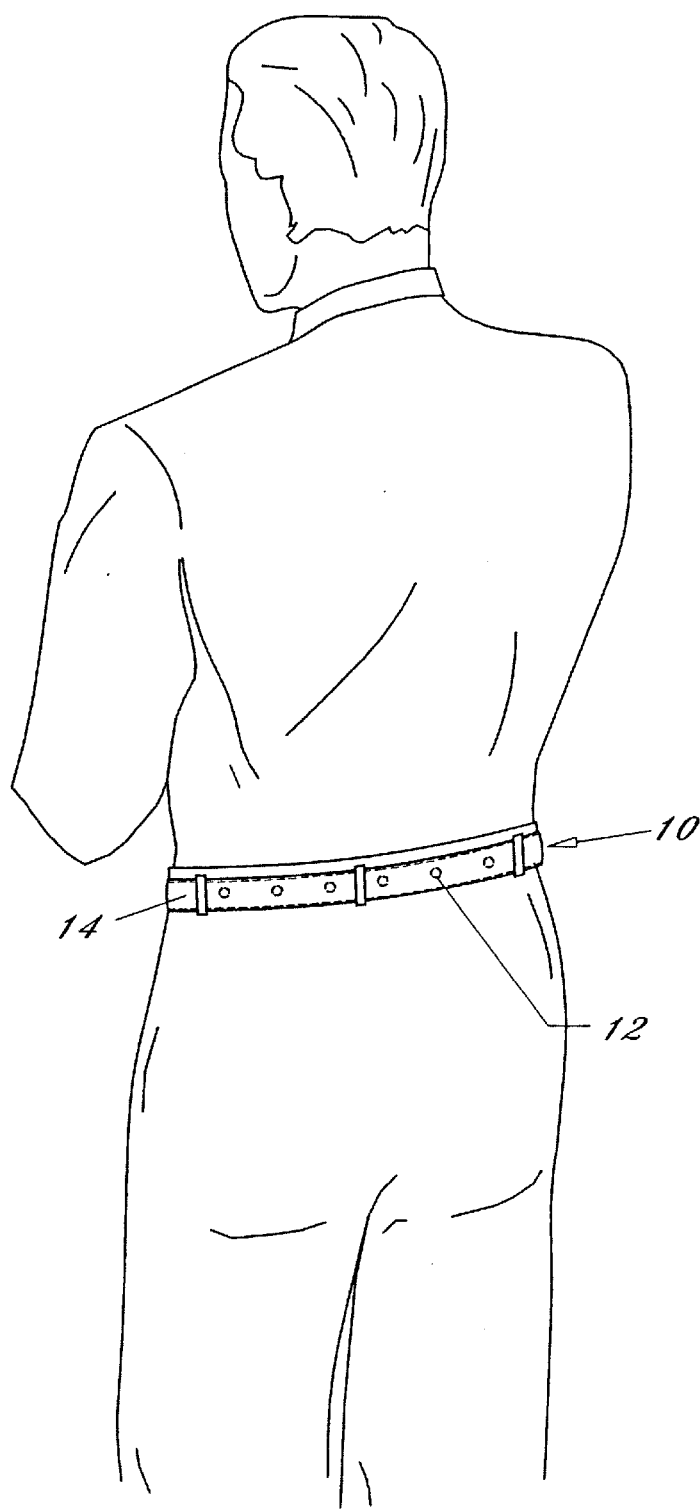
FIG. 1 shows a perspective view of the magnetic dress belt.

FIG. 1 shows the magnetic dress belt 10 of the present invention, in use, around a user's waist. The invention comprises an apparel dress belt portion 14 preferably made of leather to go around one's waist, with a plurality of magnetic disks 12 incorporated therein. FIG. 1 shows a user wearing the belt 10 around his waist, over a pair of dress pants.

The magnetic disks 12 are embedded within the leather belt portion 14 and are not visible. FIG. 1 shows the magnets for illustrative purposes only. They cannot be seen, and the belt looks exactly like a conventional dress belt.

Figure 2:
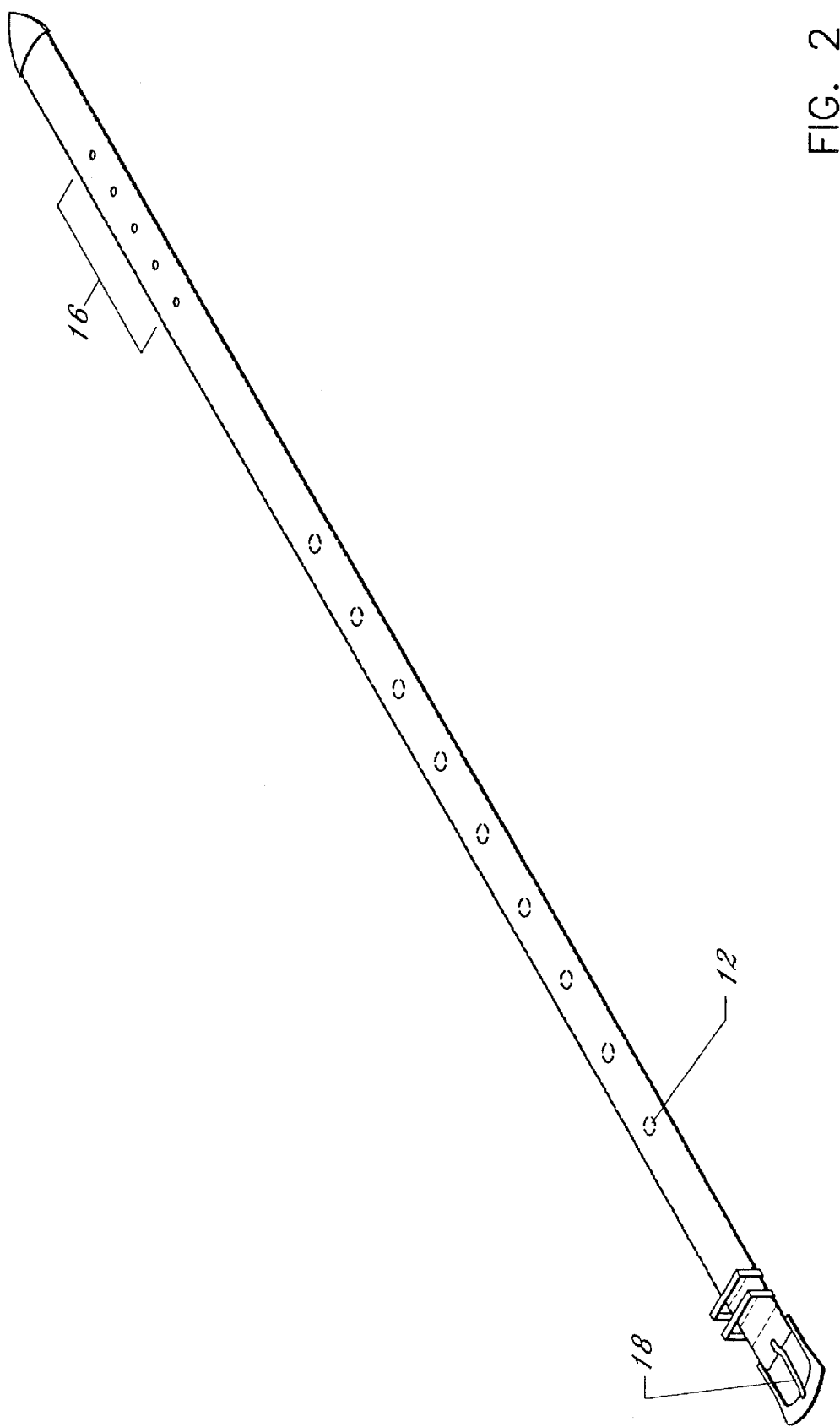
FIG. 2 shows an exploded view of the magnetic dress belt of the present invention.

FIG. 2 shows the magnetic belt 10 in a completely elongated position. It includes conventional holes 16 which receive prong 18 to secure the belt around the user's waist.

Figure 3:
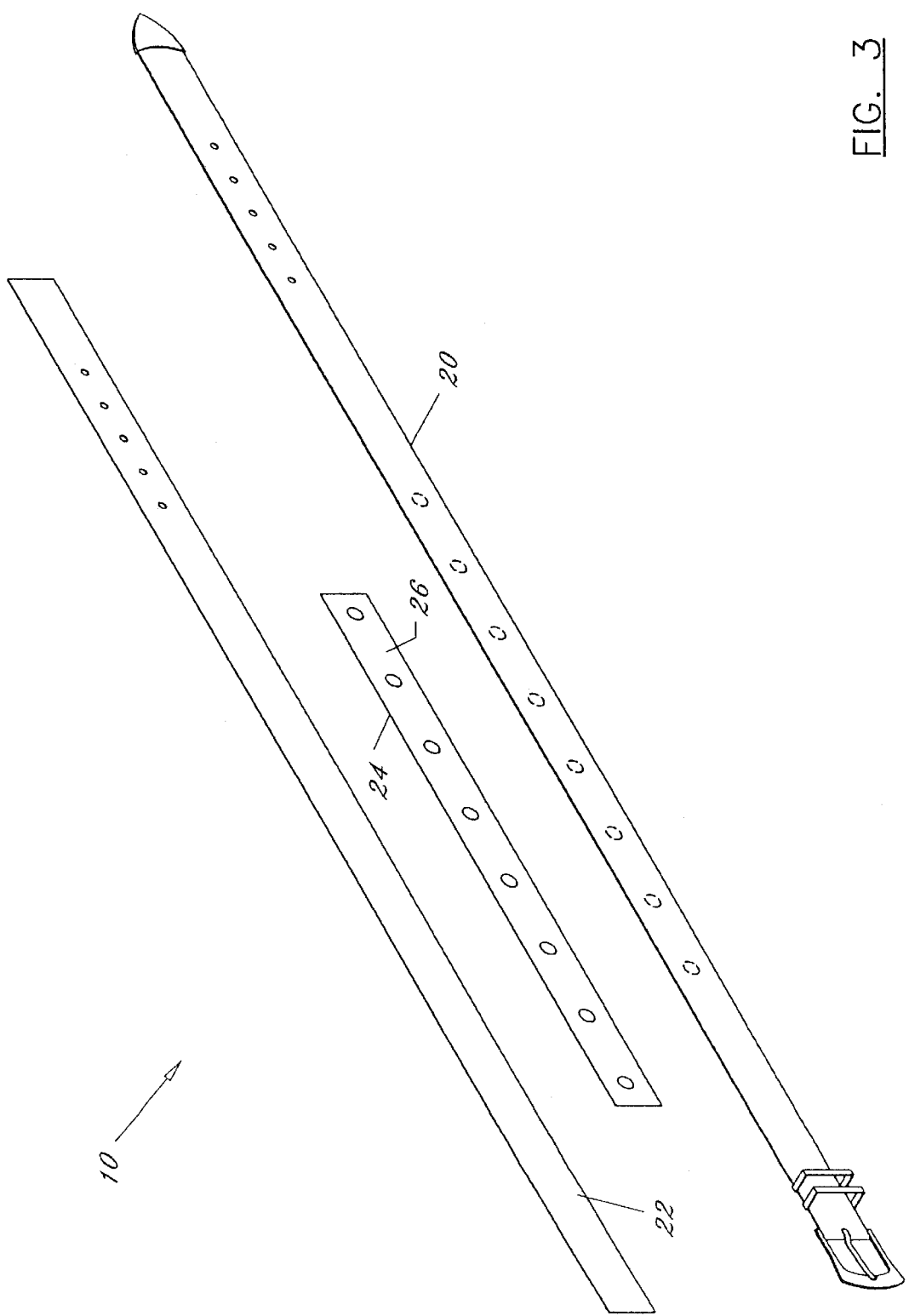
FIG. 3 shows a top cut-away view of the present invention.

FIG. 3 shows an exploded view of belt 10. Front belt portion 20 is generally comprised of leather. Back belt portion 22 and front portion 20 provide a "sandwich" around middle belt portion 24. Back portion 22 is also generally made of leather.

Middle portion 24 is comprised of a material such as foam, 26 around magnet disks 12. The magnetic disks are a combination of Neodymium nickel-plated or Ceramic magnetic disks. In one embodiment, there are fourteen (14) ceramic magnetic disks and six (6) Neodymium nickel-plated magnetic disks. Alternatively, there may be one long flexible magnet embedded between the front portion 20 and the back portion 22. Neodymium is one of the strongest permanent magnets made. It provides a great amount of magnetic field penetration. It has a manufacturers Gauss Rating of 10,800.

Ceramic magnetic disks also provide exceptional magnetic penetration. They have a manufacturer's Gauss rating of 3,800.

In the preferred embodiment, Neodymium and Ceramic magnets are used. Neodymium and Ceramic magnets are magnets that never lose their magnetic strength. They are placed in and around material 26, which is placed between leather front belt portion 20 and leather back portion 22. The front and back leather portions are sewn together leaving the magnets inside and between the leather portions.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A magnetic belt to be worn around a user's waist for providing therapeutic relief comprising:
   a flexible belt adapted to be wrapped around a user's waist; and
   one or more magnets spacially embedded throughout the substantial lengthwise interior of said belt wherein said one or more magnets are not visible and provide even and uniform magnetic therapy to the user's lower back, waist and abdomen, said magnets are a combination of Neodymium nickel-plated and ceramic magnetic disks.

2. The belt of claim 1 wherein said magnets comprise fourteen ceramic magnetic disks and six Neodymium nickel-plated magnetic disks.

3. A method for providing uniform magnetic therapeutic relief to a wearer's lower back, waist and abdomen comprising the steps of:
   providing a flexible belt adapted to be wrapped around a user's waist; and
   inserting one or more magnets within said belt wherein said magnets are spacially and uniformly embedded throughout the substantial lengthwise interior of said belt and wherein said one or more magnets are not visible and provide even and uniform magnetic therapy to the user's lower back, waist and abdomen, said magnets are a combination of Neodymium nickel-plated and ceramic magnetic disks.

4. The method of claim 3 wherein said magnets comprise fourteen ceramic magnetic disks and six Neodymium nickel-plated magnetic disks.

5. A magnetic belt to be worn around a user's waist for providing therapeutic relief comprising:
   a flexible belt adapted to be wrapped around a user's waist; and
   one or more magnets spacially embedded throughout the substantial lengthwise interior of said belt wherein said one or more magnets are not visible and provide even and uniform magnetic therapy to the user's lower back, waist and abdomen, said magnets are comprised of either all Neodymium nickel-plated magnetic disks or all ceramic magnetic disks.

6. A method for providing uniform magnetic therapeutic relief to a wearer's lower back, waist and abdomen comprising the steps of:
   providing a flexible belt adapted to be wrapped around a user's waist; and
   inserting one or more magnets within said belt wherein said magnets are spacially and uniformly embedded throughout the substantial lengthwise interior of said belt and wherein said one or more magnets are not visible and provide even and uniform magnetic therapy to the user's lower back, waist and abdomen, said magnets are comprised of either all Neodymium nickel-plated magnetic disks or all ceramic magnetic disks.

* * * * *